United States Patent [19]

Raines

[11] Patent Number: 4,729,401

[45] Date of Patent: Mar. 8, 1988

[54] ASPIRATION ASSEMBLY HAVING DUAL CO-AXIAL CHECK VALVES

[75] Inventor: Kenneth C. Raines, Bethlehem, Pa.

[73] Assignee: Burron Medical Inc., Bethlehem, Pa.

[21] Appl. No.: 8,364

[22] Filed: Jan. 29, 1987

[51] Int. Cl.⁴ ............................................. F16K 15/14
[52] U.S. Cl. .................... 137/512; 137/854; 417/568; 604/236; 604/246
[58] Field of Search ................ 137/512, 854; 417/568; 604/186, 236, 246

[56] References Cited

U.S. PATENT DOCUMENTS

| | | | |
|---|---|---|---|
| 1,507,448 | 9/1924 | Aldrich | 417/568 X |
| 1,564,146 | 12/1925 | Soresi | 417/568 X |
| 3,119,411 | 1/1964 | Bock et al. | 137/512 X |
| 3,386,470 | 6/1968 | Goda et al. | 137/512 |
| 3,446,154 | 5/1969 | Fuchs | 417/568 X |
| 3,485,419 | 12/1969 | Taylor | 417/568 X |
| 3,572,375 | 3/1971 | Rosenberg | 137/512 |
| 3,710,942 | 1/1973 | Rosenberg | 210/136 |
| 3,886,937 | 6/1975 | Bobo et al. | 128/214 R |
| 4,084,606 | 4/1978 | Mittleman | 137/102 |
| 4,210,173 | 7/1980 | Choksi et al. | 137/512.3 |
| 4,246,932 | 1/1981 | Raines | 137/512 |
| 4,535,820 | 8/1985 | Raines | 137/854 |

Primary Examiner—Alan Cohan
Assistant Examiner—John Rivell
Attorney, Agent, or Firm—Shoemaker and Mattare, Ltd.

[57] ABSTRACT

An aspiration assembly having dual co-axial check valves for pumping medical fluids with a hypodermic syringe, the assembly having a main body with two passageways in offset relationship to each other, with the passageways coming together at a large central cavity within the main body, a central support structure mounted within the central cavity of the main body, a pair of flexible resilient valve disks engaged by the central support structure, and a body cap having an outlet passageway therein for complementarily enclosing the central cavity of the main body and for retaining the central support structure and dual valve disk in co-axial relationship.

13 Claims, 4 Drawing Figures

ASPIRATION ASSEMBLY HAVING DUAL CO-AXIAL CHECK VALVES

BACKGROUND OF THE INVENTION

1. Field of the Invention

This invention relates generally to back flow check valves for use with liquid flow in administration structures for medical purposes.

2. Description of the Prior Art

A common problem of conventional type devices is that the check valves fail to function as positively and quickly as desired. Also, in hospitals and pharmacies hypodermic syringes are frequently used in the transfer of liquid medicines. Commonly, syringe pumping systems having two check valves have been used to pump a measured dose of dilutant or medicament to a series of further receptacles, or, in some cases, even into a patient. However, a common problem with such syringe pumping systems arises in the check valve system. Numerous types of check valves have been employed in the past; however, improvement still has been desired.

Existing prior art patents which may be pertinent to the present invention are as follows:

U.S. Pat. No. 3,572,375—3/23/71—Rosenberg
U.S. Pat. No. 3,710,942—1/16/73—Rosenberg
U.S. Pat. No. 3,886,937—6/3/75—Bobo et al.
U.S. Pat. No. 4,084,606—4/18/78—Mittleman
U.S. Pat. No. 4,210,173—7/1/80—Choksi et al.
U.S. Pat. No. 4,246,932—1/27/81—Raines U.S. Pat. No. 4,246,932 is by the same inventor as the present invention, and works in a similar manner thereto. However, the dual check valves therein are in co-planar relationship rather than co-axial relationship as in the present invention. The improvement of the present invention offers a number of desirable benefits over that of the inventor's prior device.

The Bobo et al. patent discloses a common administration system as is conventional, with typical check valve arrangement as used therein.

The Rosenberg patents show typical dual check valve assemblies which are substantially different from that of the present invention.

The Choksi et al. patent shows another similar dual check valve arrangement for use in a pumping system. However, in this arrangement, one check valve has a very heavy pressure, while the other one employs a light pressure.

The Mittleman patent is another dual check valve arrangement employing an umbrella valve and a duck bill valve.

None of the known prior art devices offer the new and novel features of the present invention.

SUMMARY OF THE INVENTION

An object of the present invention is to provide an aspiration assembly having dual co-axial check valves to provide a dual valve function during administration of fluids and additional liquids in medical environments.

Another object of the present invention is to provide a double check valve assembly having such valves in co-axial relationship and including a central support and alignment structure for maintaining such relationship.

A further object of the present invention is to provide a check valve assembly for use with a hypodermic syringe in transferring medical solutions from one container to other containers and/or for direct infusion into a patient.

A still further object of the present invention is to provide two in-line check valves mounted one above the other in a valve body assembly for use in the transfer of fluids wherein one valve opens to draw fluid into the system and then closes for transfer of said fluid upon the opening of the second in-line valve.

Another further object of this invention is to provide a check valve assembly with the input passage generally in-line with and parallel to the axis of an attached syringe.

The present invention provides a number of new and novel features over check valve assemblies presently in use. A three-part construction utilizes a main body having dual passageways therein which come together in a central cavity. Mounted within the cavity is a central valve support structure, one end having a valve disk pressure point thereon and the other end having a valve disk seat therewith. A complementary closure cap for the open side of the central cavity of the main body is employed to hold the other two valve housing elements together with valve disks therewith. Sonic sealing or welding is preferably used to permanently assemble the three basic housing elements into permanent relationship. The valve disks per se are of flexible resilient rubber or rubber-like material. A suitable hypodermic syringe, tubing conduit input and output lines and couplings are employed with the overall assembly to permit it to be used in various configurations and applications.

The overall assembly is fairly easy to manufacture, in that a minimum number of component elements are employed, and the actual assembly thereof is simple and straightforward. Also, in actual use, the device has proven to be failsafe and very positive in action.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
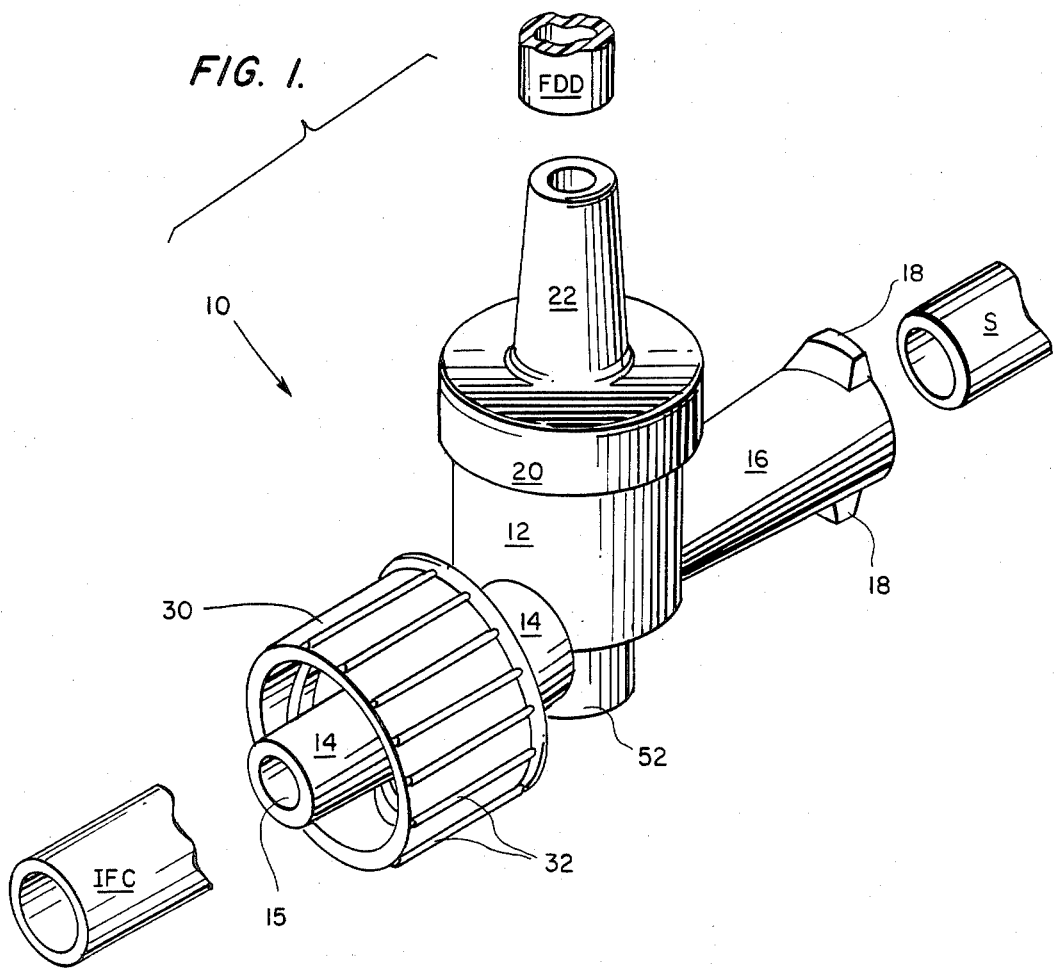
FIG. 1 is a perspective view of the present invention.
Figure 2:
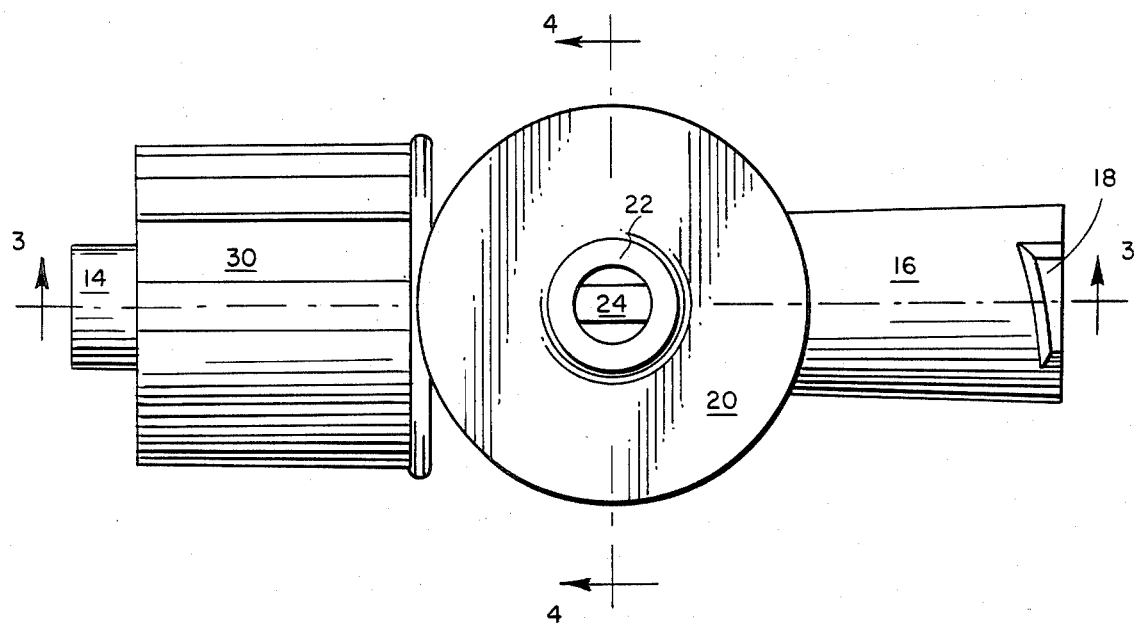
FIG. 2 is a top plan view of the invention of FIG. 1.

Referring to FIG. 1 of the drawing, reference numeral 10 indicates in general the present invention. The present invention is an aspiration assembly having dual co-axial check valves therein. A main body 12 has two extensions 14 and 16 extending oppositely therefrom. These extensions provide for passageways 15 and 17, respectively (see FIG. 3). As can be clearly seen in this figure, the inner ends of the respective passageways 15 and 17 come together in a relatively large central cavity 13 within the main body 12.

A top cap 20 is provided for closing the open upper area of the central cavity 13 within the main body 12. It should be noted that the cap 20 does not directly cap body 12, but does so through the intermediate element 42. This intermediate element 42 is a central valve disk support structure and is provided with a valve seat 41 and a valve disk triangular support and pressure point 43 mounted at the lower end of cross-rib 44.

The top cap 20 is provided with a cross-rib 23 having a triangular pressure point 24 at the middle thereof. An output passageway 21 is provided through the cap projection 22.

During assembly of the overall aspiration assembly, appropriate resilient and flexible valve disks 40 and 50 are placed within the main body 12 along with the central support structure 42. Then, sonic welding or sealing is used along the areas 55 to permanently affix the three basic components together in assembled relationship. Luer ears 18 may be provided on the projection 16 for appropriate attachment to fluid transfer apparatus, and likewise, the output projection 22 is suitably tapered externally thereof for receiving appropriate fluid dispensing devices FDD thereon. Similarly, an input fluid conduit IFC may be attached to the input projection 14 of the assembly. A coupling 30 may be provided for projection 14, with the coupling having internal threads 34 and external ribs 32. A base flange 33 is provided circumferentially of this coupling and an end 35 encloses the inner end thereof. This coupling may be retained upon projection 14 by the shoulder 18 which engages with the recess offset 36 of the coupling.

In order to positively retain the valve disk 50 in position, the main body 12 is provided with a depending bottom 52 having a pressure point 54 vertically mounted therein. Thus, as can be best visualized in the views of FIGS. 3 and 4, the lower valve disk 50 is retained in operative position by the opposite pressure points 43 and 54, while the upper valve disk 40 is suitably retained by the upper mid-surface of rib 44 and the opposite pressure point 24.

Figure 3:
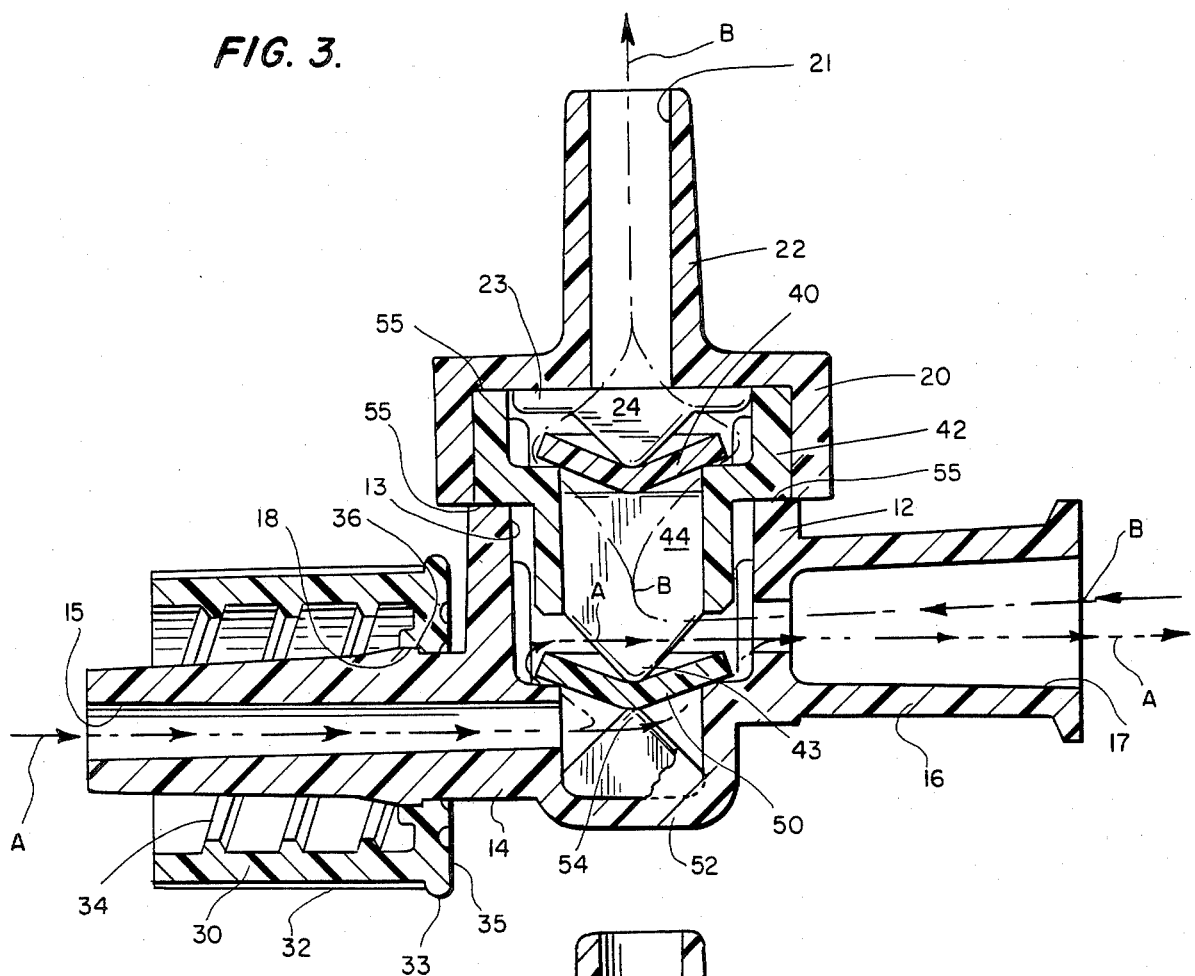
FIG. 3 is a side elevation in cross-section taken generally along lines 3—3 of FIG. 2.
Figure 4:
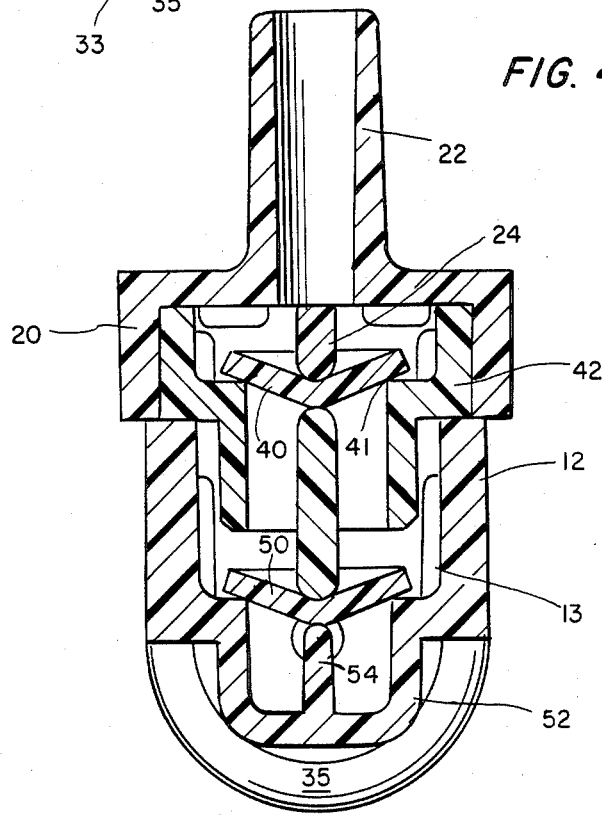
FIG. 4 is an end elevation taken in cross-section generally along lines 4—4 of FIG. 2.

As shown in FIG. 3, if a suitable hypodermic syringe S has been affixed to the projection 16, upon aspiration thereof a flow of liquid medicine can be inputted through input projection 14, as indicated by the dashed arrows A, with the lower valve disk 50 suitably opening to permit such passage thereby. Upon squeezing or compressing the syringe S, the fluid flow will reverse itself, as indicated by flow arrows B, which effects complete sealing and closure of lower valve disk 50 and simultaneously the opening of upper valve disk 40 to permit the flow as indicated out the output projection 22 into further dispensing vials and/or a patient.

The present invention with its co-axial dual valve construction offers a number of important advantages over the known prior art. The overall structure can be quickly, easily and accurately assembled and then permanently affixed together in such assembled relationship. In actual use the device is very accurate and positive and permits liquid medicament transfer and dispensing in a very precise manner. It is also more compact than many other structures and systems which are currently used for a similar purpose. The device is fairly inexpensive because it is easy to manufacture in a vertically integrated fashion—without moving the main body 12. Also, the die-cut valve disks are inexpensive as compared to molded rubber components.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A valve assembly comprising:
   a main body having two passageways therein which meet in a large central cavity within said body;
   a body cap for closing an open side of said central cavity in said main body, said cap having an outlet passageway therefrom;
   a central support structure within said central cavity of said main body;
   two co-axial valve disks mounted within said central body cavity and held in operating relationship by said central support structure; and
   said main body, said body cap and said central support structure each having a valve disk support means therewith.

2. The valve assembly of claim 1, wherein each valve disk support means comprises a pointed support with each one of said points being co-axial with the others for supporting said valve disks in said co-axial position within the main body.

3. The valve assembly of claim 2, wherein said valve disks are each made of resilient rubber material.

4. The valve assembly of claim 2, wherein said valve disks are each made of resilient rubber-like material.

5. The valve assembly of claim 2, wherein said body cap, central support and main body are permanently fastened together by sonic sealing.

6. A pumping system for medical fluids with a hypodermic syringe means connected to inlet and outlet check valves, wherein the improvement comprises:
   a valved body with an inlet passage from which pumped fluid is supplied, a syringe connecting passage, and an outlet passage, said passages being in fluid flow communication within said valved body;
   an inlet valve seat in the inlet passage;
   an outlet valve seat in a central support structure within said valved body;
   a flexible imperforate disk valve member fitted against each of the inlet and outlet valve seats;
   support posts within the valve body for respectively urging each disk valve member against its respective valve seat;
   another support post within the valve body for retaining the disk valve member of said inlet valve in operative position;
   said pair of valve members being in co-axial alignment with each other; and
   an input fluid conduit connected to the inlet passage which is adapted to attach to a medical liquid source, whereby fluid can flow from a fluid supply source through the inlet passage into the syringe on an intake stroke of the syringe and be pumped out through the outlet passage while fluid flow out through the inlet passage is blocked.

7. A T-connector housing for coupling a syringe to a liquid medicament supply for delivery to a patient via a fluid delivery device of a volume of liquid medicament, comprising, in combination, a coupling body having three interconnected passages therein; check valves in two of said passages controlling flow of fluid therethrough in a single direction, said check valves each comprising a valve member of flexible material fixedly held in the passage at one portion thereof in a leak-tight seal, and at a peripheral portion thereof engaging a valve seat or a like valve member in a relatively leak-tight seal, so as to close the passage, and adapted to crack open in a flex-action movement to a short distance away from the valve seat or like valve member, so as to open the passage; said check valves being in co-axial alignment with each other and each having a central, pressure point valve support on opposite sides thereof and means in an outer portion of each passage adapted for connection of the passage and coupling to at least one of a liquid medicament supply, a fluid delivery device, a syringe and interconnecting tubing; the body being formed of plastic, and the valves being held therein permanently as one unit.

8. A T-connector valve according to claim 7, in which the flexible material of the valves is resilient rubber material.

9. A T-connector valve according to claim 7, in which the flexible material of the valves is a resilient rubber-like material.

10. A valve assembly comprising:
- a main body having two passageways therein which meet at a large central cavity within said body, said cavity having a central pressure point and a valve seat;
- a body cap for closing an open side of said central cavity in said main body, said cap having an outlet passageway therefrom and a central pressure point therewith;
- a central support structure within said central cavity of said main body, said support structure having a valve seat and a central pressure point therewith; and
- two resilient valve means mounted within said central body cavity which are maintained in cooperating co-axial relationship by said central support structure.

11. The valve assembly of claim 10, wherein said pressure points each comprise a pointed triangular support with all of said points and valve seats being co-axial with each other for supporting said valve means in co-axial relationship with the central cavity of said main body.

12. The valve assembly of claim 11, wherein said valve means comprise valve disks each made of resilient, flexible material.

13. The valve assembly of claim 12, wherein said main body, body cap and central support structure are permanently fastened together by sonic sealing.

* * * * *